United States Patent
Dordoni et al.

(10) Patent No.: US 7,321,679 B2
(45) Date of Patent: Jan. 22, 2008

(54) MACHINE FOR INSPECTING GLASS BOTTLES

(75) Inventors: Joe J. Dordoni, Watkins Glen, NY (US); Sarath G. Tennakoon, Elmira, NY (US); Michael M. Rentschler, Burdett, NY (US); Richard D. Diehr, Horseheads, NY (US); Kee Sin Loo, Singapore (SG)

(73) Assignee: Emhart Glass SA, Cham (CH)

( * ) Notice: Subject to any disclaimer, the term of this patent is extended or adjusted under 35 U.S.C. 154(b) by 749 days.

(21) Appl. No.: 10/883,885

(22) Filed: Jul. 2, 2004

(65) Prior Publication Data

US 2006/0008133 A1  Jan. 12, 2006

(51) Int. Cl.
*G06K 9/00* (2006.01)
(52) U.S. Cl. .................................................. 382/142
(58) Field of Classification Search ................ 382/142; 427/262, 266, 267, 274
See application file for complete search history.

(56) References Cited

U.S. PATENT DOCUMENTS

| | | | | | |
|---|---|---|---|---|---|
| 3,180,994 | A | * | 4/1965 | Rottmann | 356/428 |
| 4,691,231 | A | * | 9/1987 | Fitzmorris et al. | 348/127 |
| 5,351,306 | A | * | 9/1994 | Finkler et al. | 382/169 |

FOREIGN PATENT DOCUMENTS

EP  0655610  5/1995

* cited by examiner

*Primary Examiner*—Daniel Miriam
*Assistant Examiner*—G. F. Cunningham
(74) *Attorney, Agent, or Firm*—Spencer T. Smith

(57) ABSTRACT

A glass container inspection machine is disclosed for inspecting glass stippled bottles for defects. Stippled bottles are supported at an inspection station and are illuminated with a light source. The stippled bottle is imaged a pixel matrix with the pixels of the image varying in intensity from bright to gray at the points of stippling. A computer evaluates the pixels of the image including a look up table for values to be assigned to specific light intensities from light to black, the plot of the look up table having a high gain portion from black to gray and a continuous low gain portion from gray to white.

1 Claim, 1 Drawing Sheet

MACHINE FOR INSPECTING GLASS BOTTLES

BACKGROUND OF THE INVENTION

The present invention relates to machines which inspect glass bottles for defects which could have occurred in the forming process. A light source directs light through the sidewalls of the bottle and imperfections will interfere with the light rays. For example, should a wall have a blister, the blister may change the direction of the light rays passing therethrough and as a result these rays may not reach the viewing medium such as a CCD camera causing the blister to look black. Such blackness would indicate a defect.

Critical to the inspection process is the comparison of adjacent pixels in the camera by a computer which compares the light intensity of these pixels. When adjacent pixels progress from light to dark, the computer recognizes that there is an edge and its evaluation may define the edge as the edge of a defect.

Some bottle surfaces are formed with stippling, (lots of small bumps) on the surface (stippling can be generalized to various kinds of embossing). Stippling appears as grey spots in the image, which when edge detected is detected as a significant enough change to mask defects even though they may be darker or have sharper edges. The grey spots are the result of a loss of light getting to the camera because the stippling has acted like a lens to spread that light out and so only a part of the light passing through there gets to the camera. Around the stippling the light is not being dispersed and so appears brighter to the camera.

OBJECT OF THE INVENTION

It is accordingly an object of the present invention to provide a way of locating defects associated with the wall of a bottle which has been stippled.

Other objects and advantages of the present invention will become apparent from the following portion of this specification and from the accompanying drawings which illustrate, in accordance with the mandate of the patent statutes, a presently preferred embodiment incorporating the principles of the invention.

BRIEF DESCRIPTION OF THE PREFERRED EMBODIMENT

Figure 1:
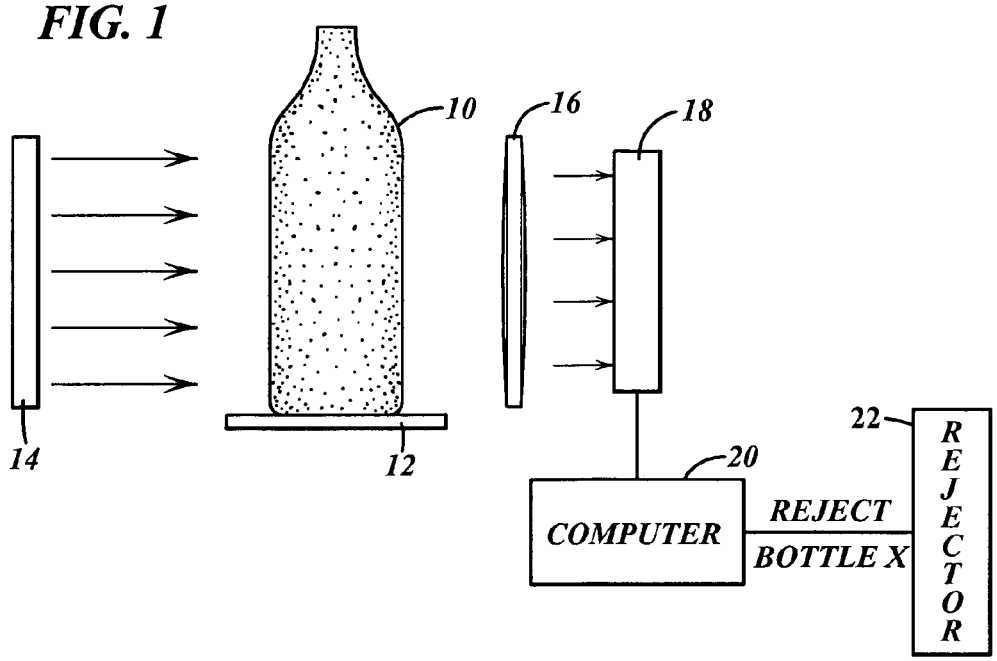
FIG. 1 is a schematic illustration of a machine for inspecting bottles.

An inspection machine is schematically disclosed in FIG. 1. A glass bottle 10 is conveyed through the inspection machine via a conveyor 12. During this transit the bottle is located at an inspection station which includes a light source 14, which directs light towards the stippled bottle and the light which passes through the bottle is focused by a suitable lens 16 onto the imaging area of a CCD camera or the like 18. The computer 20 scans the pixels, comparing the brightness of adjacent pixels and when the change reaches a defined limit, the computer determines that there is a defect and issues a Reject Bottle X signal to a rejector 22. The light source may be plane or curved.

Figure 2:
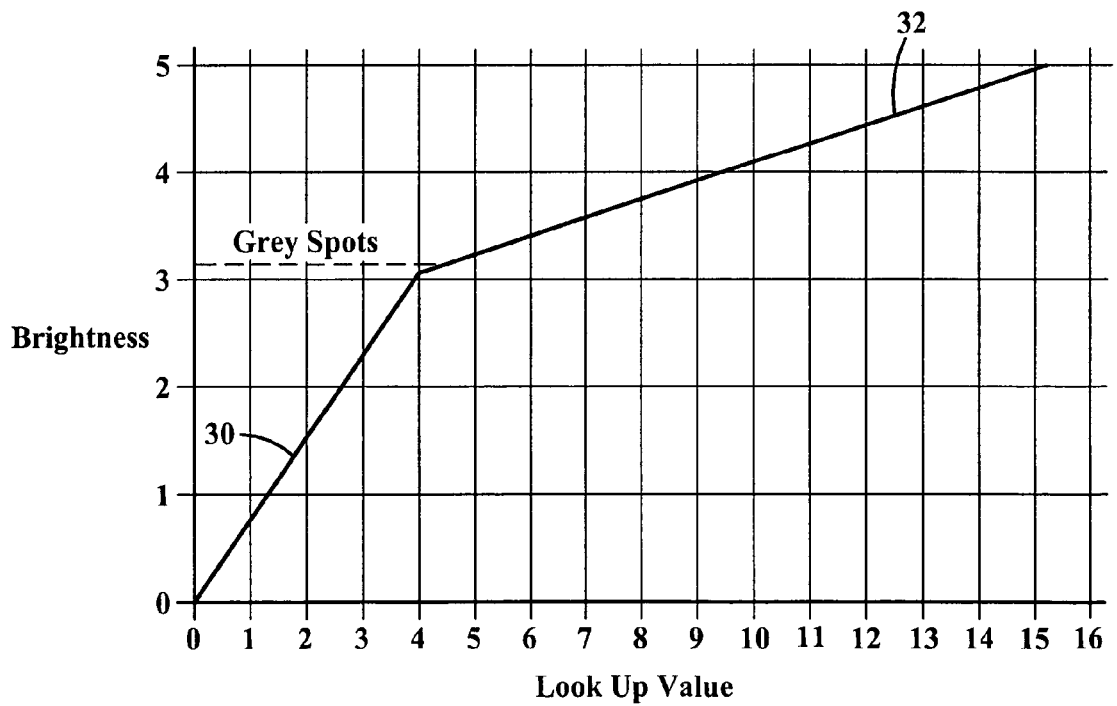
FIG. 2 is a Look Up Table for use in the inspection machine computer disclosed in FIG. 1.

FIG. 2 is a plot of brightness (Y-axis), black being 0 and white being 5 versus look up value (X-axis). The plot has a high gain portion 30 from black to an intensity just below the intensity of a grey portion of the stippling, and a low gain portion 32 which continues the plot from this point. As shown, equal changes in light intensity in the high and low gain portions of the plot (1 unit for example in the Y-axis), produce drastically different changes in the Y-axis. By applying a look up table that compresses the number of grey shades between the grey spots of the stippling and the white around them, the edge detection (rate of change in the grey shade from one pixel to the next) algorithm will produce a larger step change for the defect than for the grey stippling spots. In other words, a change from gray towards black will have about eight times the weight as a change from gray towards white and the gray spots will therefore not mask black defects.

The invention claimed is:

1. A machine for inspecting glass stippled bottles for defects comprising
   an inspection station including
      means for supporting a stippled bottle for inspection,
      a light source for illuminating a stippled bottle supported at the inspection station,
      imaging means for imaging the illuminated stippled bottle on a pixel matrix, the pixels of the image varying in intensity from bright to gray at the points of stippling,
   computer means for evaluating the pixels of the image including a look up table for values to be assigned to specific light intensities from light to black, the plot of said look up table having a high gain portion from black to gray and a continuous low gain portion from gray to white.

* * * * *